United States Patent [19]

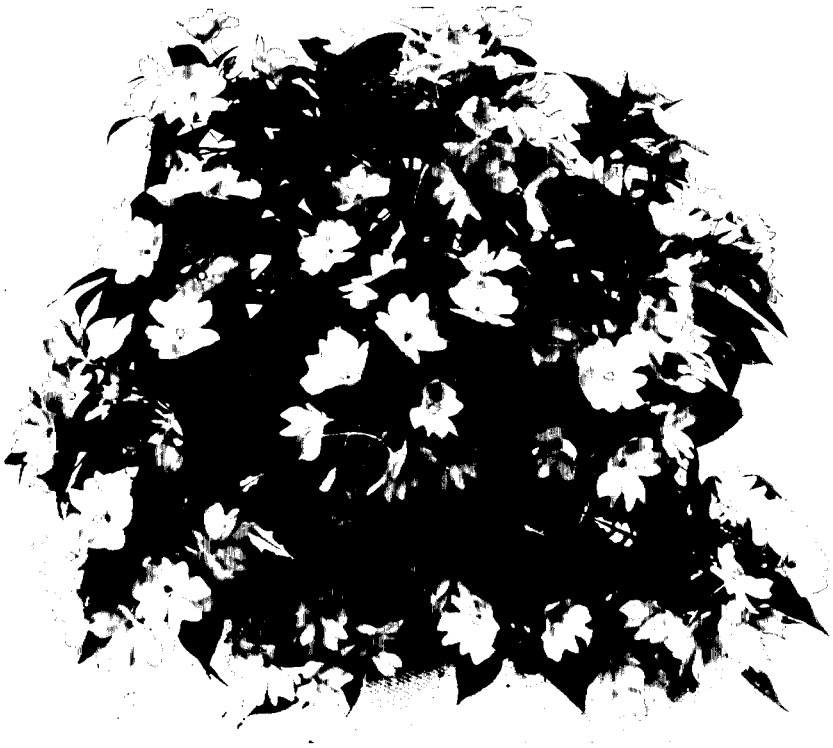

Mikkelsen

[11] Patent Number: Plant 5,783

[45] Date of Patent: Aug. 19, 1986

[54] IMPATIENS PLANT NAMED PULSAR

[75] Inventor: James C. Mikkelsen, Ashtabula, Ohio

[73] Assignee: Mikkelsens, Inc., Ashtabula, Ohio

[21] Appl. No.: 664,399

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Pulsar, having compact plant size and vigorous self-branching growth habit, distinct cherry-red flowers, multiple flowering from the leaf axils, extremely floriferous nature of plant, good keeping quality of flowers, and by its adaptability to various environments of use.

1 Drawing Figure

The present invention relates to a new and distinctive cultivar of New Guinea Impatiens plant, botanically known as *Impatiens,* and referred to by the cultivar name Pulsar.

Pulsar was developed by me in Ashtabula, Ohio, through controlled breeding by crossing Mikkelsen Seedling No. 82-MISC-1 (seed parent)×Mikkelsen Seedling No. 82-521-1 (pollen parent). Asexual reproduction by terminal or stem cuttings of the progeny of the stated cross in Ashtabula, Ohio, has shown that the unique features of this new Impatiens are stabilized and are reproduced true to type in successive propagations.

The following characteristics distinguish the new impatiens from both its parent varieties and other cultivated impatiens of this type known and used in the floriculture industry:

1. Larger, more vigorous growing plant than the cultivars Comet and Quasar, disclosed in my copending applications, and Solared, disclosed in U.S. Plant Pat. No. 5,131. It is similar to Dawn, also disclosed in my pending application, and Cosmos, U.S. Plant No. 5,153, in size and growth habit, and is more compact than Corona, disclosed in U.S. Plant Pat. No. 5,184.

2. Flower color is unique cherry-red which is much brighter than Corona or Cosmos.

3. Flower is larger than Cosmos and Solared, is similar in size to Quasar and Dawn, but is not as large as Zenith, a further cultivar of the present inventor described in a pending application.

4. Flowers have excellent keeping qualities, and are found both below and above the foliage, much like Comet and Quasar, due to the multiple flowering at the leaf axils.

5. The new cultivar has an excellent self-branching habits, which together with its vigorous growth habit, provides a semi-mound form ideal for pots, hanging baskets and bedding plant use.

6. Plants and flowers have good low temperature tolerance as demonstrated by exposure to two (2) nights of 2.2° C. after planting out in early May and being able to keep growing and flowering.

7. Flowering begins earlier than Cosmos and Corona, and is similar in flowering to Comet and Quasar both in earliness and amount of flowers.

8. Foliage color is deeper green than Columbia, disclosed in U.S. Plant Pat. No. 5,126, or Solared. It is similar to Gemini and Comet in color, but has less variegation at the midrib than Gemini and Comet and is smaller in size.

9. Cultivar would be excellent for further hybridization work for the multiple flowering habit in this distinct color on a compact plant for pot plant use.

The accompanying colored photograph taken in March 1984 illustrates the overall appearance in perspective view of Pulsar, and showing the colors as true as it is reasonably possible to obtain in a colored reproduction of this type.

The following is a detailed description of my new Impatiens cultivar based on plants produced under commercial practices in Ashtabula, Ohio, grown in 5.5" green plastic pots during the winter of 1983–1984, and describes colors under reduced sunlight and early floriferous flowering in an adverse environment. Color references are made to The Royal Horticultural Society Colour Chart except where general terms of ordinary dictionary significance are used.

Parentage: Mikkelsen Seedling No. 82-MISC-1×Mikkelsen Seedling No. 82-521-1.

Propagation:

(A) *Type cutting.*—Stem 15 mm long will develop to 4 to 5 cm long in 18–21 days.

(B) *Time to root.*—8–10 days at 23° C. summer, and 1&0–12 days at 20° C. winter.

(C) *Rooting habit.*—Large mass of fiberous roots from the stem.

Plant description:

(A) *Form.*—Symmetrical, semi-mounded, compact, vigorously flowering herb.

(B) *Habit of growth.*—Vigorous, self-branching, compact, pale red stems, continuous flowering.

(C) *Foliage description.*—Large dark green leaves with variegation at midrib, and central veins red. (1) Size: 10 to 11 cm long by 3.75 to 4 cm wide on mature leaf. (2) Shape: Lanceolate to ovate with acuminate apex, acute base. (3) Texture: Rugose upper side, glabrous under side. (4) Margin: Serrated, finely ciliated. (5) Color: Young foliage, top side 146A, under side 183C. Mature foliage, top side 147A, under side 183A. (6) Venation: Pinnate, midrib vein is red.

Flowering description:

(A) *Flowering habits.*—Flowers continuously from leaf whorl in semi-progressively and orderly manner (number of flowers per leaf axil vary from 1 to 3 with some having 2 flowers per pedicel.) Takes 5 to 7 days from buds showing color to bloom; flowers last 2 to 3 weeks.

(B) *Natural flowering season.*—Indeterminate and continuous. Quantity of flowers increases with increasing levels of light intensity and duration.

(C) *Flower buds.*—Ellipsoidal, flowers perfect, reddish spur 5.5 to 6.0 cm long on mature bud with throat behind ovary and originating from the major sepal.

(D) *Flowers borne.*—On individual short pedicels from whorl of 3 to 7 leaves, increasing in number as plant ages, but not consistent on branches of plant. Flowers semi-progressively around the whorl as leaves and buds develop (again inconsistent as it varies from 1 to 3 flowers per leaf axil); flowers are from above to inside canopy.

(E) *Quantity of flowers.*—Very floriferous, flowering continuous so that tight buds to mature blooms are visible at the same time in large numbers.

(F) *Petals.*—(1) Shape: Heart shaped, top petal dominant, 4 overlapping and symmetrical. (2) Color: Top side in winter when opening 61B, fading to 67A and toward 63B; under side 53C to 53D. (3) Number of petals: Five (5) in number. (4) Size of flowers: 6 to 7 cm.

(G) *Reproductive organs.*—(1) Stamens: Five (5) in number. (a) Anther shape: Hooded, color 58C. (b) Pollen color: Cream. (2) Pistils (a) Stigma shape: 5, segmented column, reddish in color. (b) Style color: Clear. (c) Ovaries: Five (5) in number, celled, 5.5 mm, until fertilized reddish green in color.

Disease resistance:

No significant disease or insect problems have been seen to date.

Summary of important characteristics of new cultivar:

1. Distinct new cherry-red color.
2. Multiple flowering at leaf axil.
3. Semi-mounded, compact growth habit.
4. Extremely floriferous cultivar.

I claim:

1. A new and distinct cultivar of New Guinea Impatiens plant named Pulsar, as described and illustrated, and particularly characterized by its compact plant size and vigorous self-branching growth habit, distinct cherry-red flowers, multiple flowering from the leaf axils, extremely floriferous nature of plant, good keeping quality of flowers, and by its adaptability to various environments of use.

* * * * *